(12) United States Patent
Okada

(10) Patent No.: US 12,245,783 B2
(45) Date of Patent: Mar. 11, 2025

(54) ENDOSCOPIC TREATMENT TOOL

(71) Applicant: OLYMPUS CORPORATION, Tokyo (JP)

(72) Inventor: Tsutomu Okada, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 878 days.

(21) Appl. No.: 17/350,309

(22) Filed: Jun. 17, 2021

(65) Prior Publication Data
US 2021/0307768 A1 Oct. 7, 2021

Related U.S. Application Data

(63) Continuation of application No. PCT/JP2018/047830, filed on Dec. 26, 2018.

(51) Int. Cl.
*A61B 17/221* (2006.01)
*A61B 17/00* (2006.01)

(52) U.S. Cl.
CPC .. *A61B 17/221* (2013.01); *A61B 2017/00296* (2013.01); *A61B 2017/00323* (2013.01);
(Continued)

(58) Field of Classification Search
CPC ............ A61B 17/00234; A61B 17/221; A61B 17/22031; A61B 17/32056; A61B 17/32075; A61B 2017/00296; A61B 2017/00323; A61B 2017/00358; A61B 2017/00862; A61B 2017/00867; A61B 2017/2212; A61B 2018/141; A61B 1/307
(Continued)

(56) References Cited

U.S. PATENT DOCUMENTS

| 4,691,705 A | 9/1987 | Okada |
| 4,741,335 A | 5/1988 | Okada |

(Continued)

FOREIGN PATENT DOCUMENTS

| EP | 0 152 032 A2 | 8/1985 |
| EP | 3 081 177 A1 | 10/2016 |

(Continued)

OTHER PUBLICATIONS

US Office Action issued Apr. 14, 2022 received in U.S. Appl. No. 17/131,880.

(Continued)

*Primary Examiner* — Kankindi Rwego
(74) *Attorney, Agent, or Firm* — Scully, Scott, Murphy & Presser, P.C.

(57) ABSTRACT

Provided is an endoscopic treatment tool including: a sheath that has a longitudinal axis; a first operation wire and a second operation wire that are inserted through the sheath so as to be able to be moved forward and backward; a treatment part constituted by a first wire rod and a second wire rod that have lower bending rigidity than bending rigidity of the second operation wire; a first joint part inside which the second wire rod passes and that joins a distal-end section of the first operation wire and a proximal-end section of the first wire rod; and a second joint part that joins a distal-end section of the second operation wire and a proximal-end section of the second wire rod.

19 Claims, 16 Drawing Sheets

(52) U.S. Cl.
CPC ............... *A61B 2017/00862* (2013.01); *A61B 2017/00867* (2013.01)

(58) Field of Classification Search
USPC .................................................. 606/113, 127
See application file for complete search history.

(56) References Cited

U.S. PATENT DOCUMENTS

| | | | |
|---|---|---|---|
| 5,059,199 A | | 10/1991 | Okada et al. |
| 5,064,428 A | * | 11/1991 | Cope .................... A61B 17/221 |
| | | | 606/127 |
| 5,562,678 A | * | 10/1996 | Booker ................ A61B 17/221 |
| | | | 606/127 |
| 6,013,086 A | | 1/2000 | Ouchi et al. |
| 6,077,274 A | | 6/2000 | Ouchi et al. |
| 6,187,017 B1 | | 2/2001 | Gregory, Jr. |
| 6,468,285 B1 | | 10/2002 | Hsu et al. |
| 2002/0091394 A1 | | 7/2002 | Reynolds et al. |
| 2004/0116941 A1 | | 6/2004 | Reynolds et al. |
| 2010/0106164 A1 | | 4/2010 | Reynolds et al. |
| 2016/0192957 A1 | | 7/2016 | Okada |
| 2017/0156745 A1 | | 6/2017 | Okada |

FOREIGN PATENT DOCUMENTS

| | | |
|---|---|---|
| EP | 3 318 205 A1 | 5/2018 |
| JP | S56-109705 U | 8/1981 |
| JP | S60-096241 A | 5/1985 |
| JP | S60-242848 A | 12/1985 |
| JP | S62-014811 Y2 | 4/1987 |
| JP | S62-014812 Y2 | 4/1987 |
| JP | S62-041724 B2 | 9/1987 |
| JP | S63-020140 B2 | 4/1988 |
| JP | H03-231654 A | 10/1991 |
| JP | H05-000116 U | 1/1993 |
| JP | H06-133978 A | 5/1994 |
| JP | H09-168543 A | 6/1997 |
| JP | H11-047141 A | 2/1999 |
| JP | H11-099157 A | 4/1999 |
| JP | 2000-126193 A | 5/2000 |
| JP | 2002-017739 A | 1/2002 |
| JP | 2004-516880 A | 6/2004 |
| JP | 2005-021195 A | 1/2005 |
| JP | 2006-314715 A | 11/2006 |
| JP | 2013-022386 A | 2/2013 |
| JP | 2015-116399 A | 6/2015 |
| WO | 02/053037 A2 | 7/2002 |
| WO | 2015/087952 A1 | 6/2015 |
| WO | 2017/002438 A1 | 1/2017 |
| WO | 2020/003435 A1 | 1/2020 |

OTHER PUBLICATIONS

Chinese Office Action dated Sep. 27, 2023 received in 201880094848.1.
Zeon Medical Inc., Zemex Crusher Catheter M_Product information, Retrieved from the Internet in Aug. 2020, URL: https://www.zeonmedical.co.jp/product/digestive/crusher_catheter/index_01.html.
Boston Scientific Corporation, StoneSmash_Product information, Retrieved from the Internet in Aug. 2020, URL: https://www.bostonscientific.com/jp-JP/products/basket/StoneSmash.html.
U.S. Appl. No. 17/131,880, filed Dec. 23, 2020.
International Search Report and Written Opinion of the International Searching Authority dated Aug. 28, 2018 received in PCT/JP2018/024582.
International Search Report dated Mar. 19, 2019 received in PCT/JP2018/047830.

* cited by examiner

ENDOSCOPIC TREATMENT TOOL

CROSS-REFERENCE TO RELATED APPLICATIONS

This is a continuation of International Application PCT/JP2018/047830, with an international filing date of Dec. 26, 2018, which is hereby incorporated by reference herein in its entirety.

TECHNICAL FIELD

The present invention relates to an endoscopic treatment tool.

BACKGROUND ART

There are known basket forceps as a means for removing gallstones generated in the bile duct from the common bile duct (for example, see PTL 1).

The basket forceps have: a basket in which a plurality of elastic wires are joined at two places, i.e., at a distal-end tip and at a first joint part, so as to be formed in a basket shape therebetween; and at least one operation wire to which the elastic wires, which extend toward the proximal end beyond the first joint part, are joined at a joint section of a second joint part.

The operation wire is required to have higher rigidity than the elastic wires. On the other hand, low rigidity is required in a section between the first joint part and the second joint part because this section corresponds to a position that interferes with a bending section and a forceps elevator of the endoscope when used while being disposed inside a channel of an endoscope.

In the basket forceps of PTL 1, at least one of the elastic wires is made to extend toward the proximal end beyond the second joint part, thereby preventing the basket from falling off due to breakage of the second joint part.

Furthermore, in a case in which stainless wires are used as the elastic wires and the operation wire, the first joint part and the second joint part can be joined through brazing.

CITATION LIST

Patent Literature

{PTL 1} Japanese Examined Utility Model Application, Publication No. Sho 62-14811

SUMMARY OF INVENTION

One aspect of the present invention is directed to an endoscopic treatment tool including: a sheath that has a longitudinal axis; a first operation wire and a second operation wire that are inserted through the sheath so as to be able to be moved forward and backward; a treatment part constituted by a first wire rod and a second wire rod that have lower bending rigidity than bending rigidity of the second operation wire; a first joint part inside which the second wire rod passes and that joins a distal-end section of the first operation wire and a proximal-end section of the first wire rod; and a second joint part that joins a distal-end section of the second operation wire and a proximal-end section of the second wire rod.

Another aspect of the present invention is directed to an endoscopic treatment tool including: a sheath that has a longitudinal axis; a first operation wire and a second operation wire that are inserted through the sheath so as to be able to be moved forward and backward; a treatment part constituted by a first wire rod and a second wire rod that have lower bending rigidity than bending rigidity of the second operation wire; a first joint part that joins a distal-end section of the first operation wire and a proximal-end section of the first wire rod; and a second joint part inside which the first operation wire passes and that joins a distal-end section of the second operation wire and a proximal-end section of the second wire rod.

DESCRIPTION OF EMBODIMENT

An endoscopic treatment tool 1 according to one embodiment of the present invention will be described below with reference to the drawings.

Figure 1:
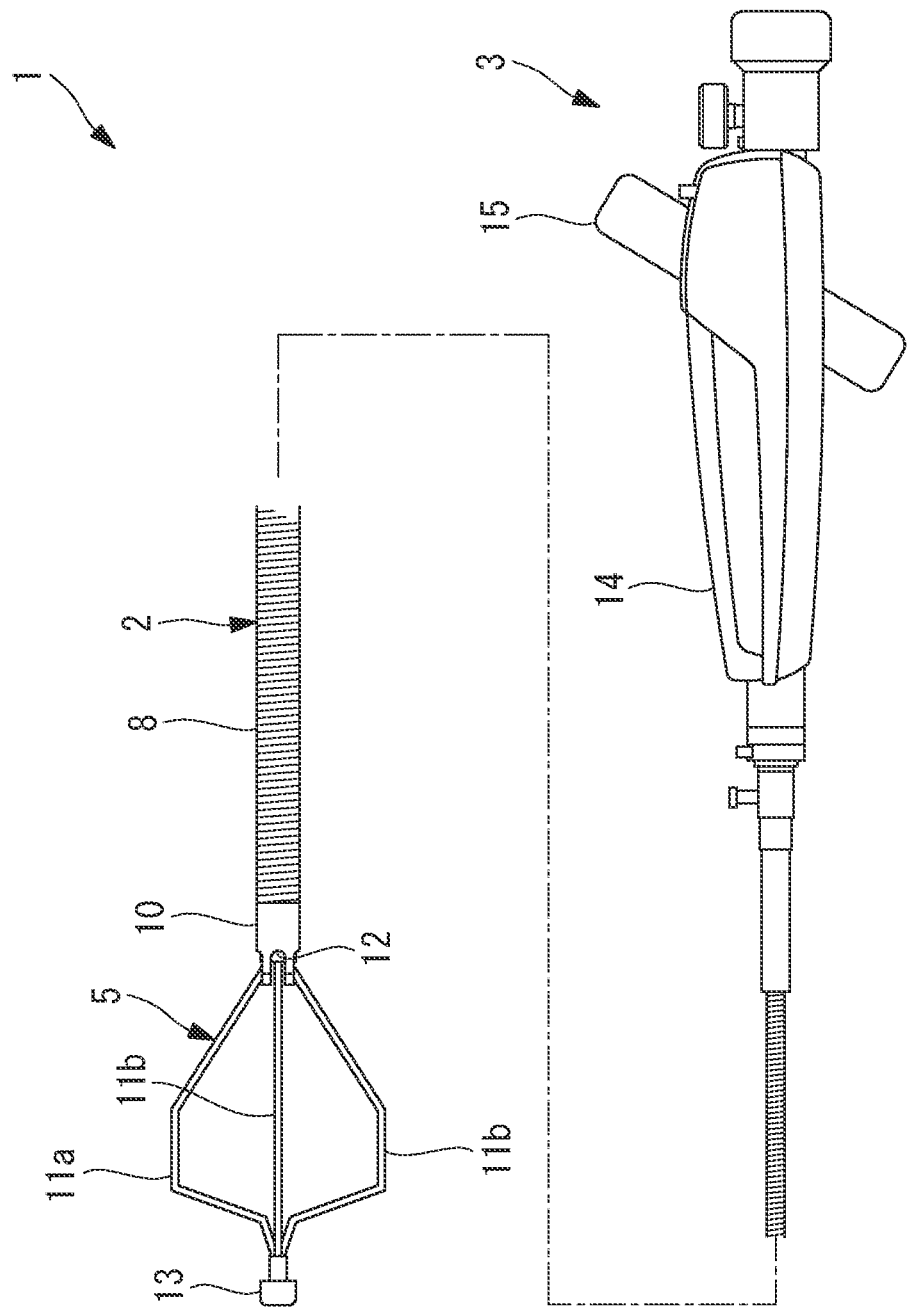
FIG. 1 is a schematic view showing an endoscopic treatment tool according to one embodiment of the present invention.
Figure 2:
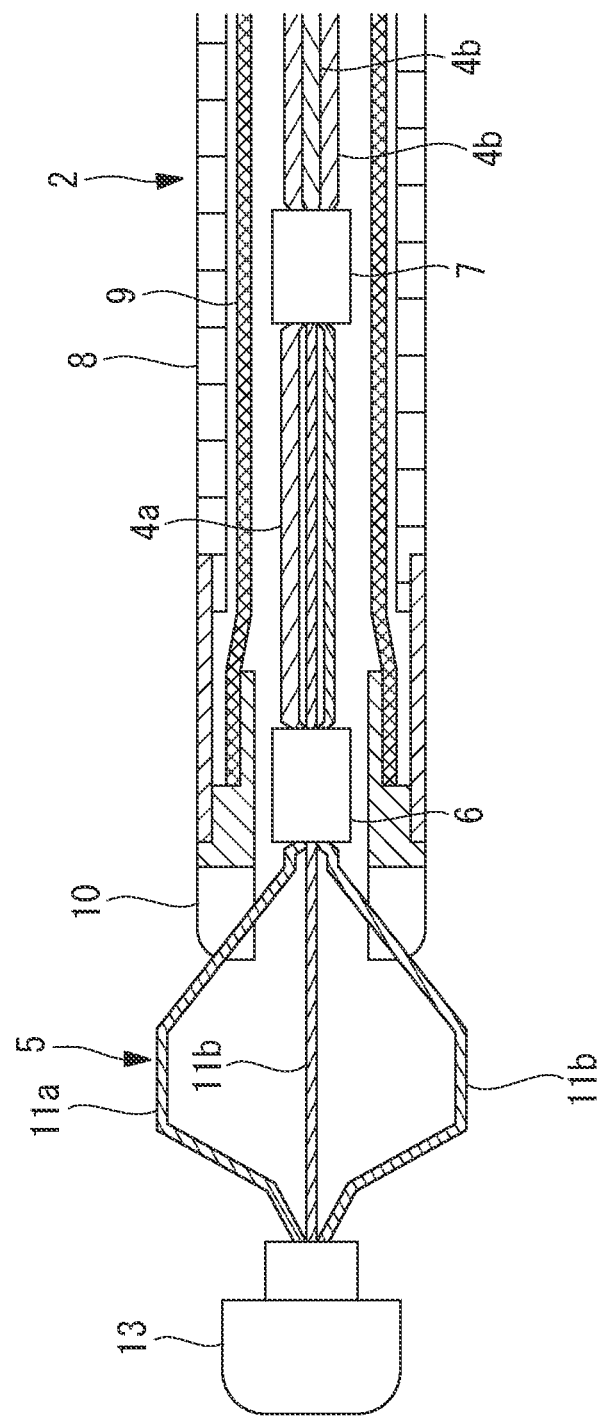
FIG. 2 is a longitudinal sectional view showing a sheath, a basket, and operation wires of the endoscopic treatment tool shown in FIG. 1.

As shown in FIGS. 1 and 2, the endoscopic treatment tool 1 of this embodiment is basket forceps and includes: a flexible sheath 2 that can be inserted through a channel of an endoscope (see FIG. 11) 100; an operation part 3 that is connected to a proximal end of the sheath 2; operation wires 4a and 4b that are inserted through the sheath 2 so as to be able to be moved forward and backward in the longitudinal direction; and a basket (treatment part) 5 that is attached to distal ends of the operation wires 4a and 4b. The operation wires 4a and 4b and the basket 5 are joined by a first joint part 6 and a second joint part 7 that are disposed apart from each other in the longitudinal direction of the operation wires 4a and 4b.

As shown in FIG. 2, the sheath 2 includes a coil sheath 8 that is formed by densely winding a metal flat plate, a tube sheath 9 that covers an inner circumferential surface of the coil sheath 8, and a distal-end cover 10 that is brazed at a distal end of the coil sheath 8.

The tube sheath 9 is formed of a resin tube and is inserted between the metal coil sheath 8 and the metal operation wires 4a and 4b, thereby making it easier for the basket 5 and the operation wires 4a and 4b to move in the longitudinal direction and making it easier for the basket 5 to open and close.

The distal-end cover 10 is formed of a ring metal, and recessed regions 12 that can receive elastic wires 11a and 11b constituting the basket 5 are formed in a distal-end section of the distal-end cover 10 at four places at intervals in the circumferential direction. When a gallstone is to be crushed, the elastic wires 11a and 11b are inserted into the recessed regions 12, and a tightening force at the operation part 3 is applied to the elastic wires 11a and 11b, which pass inside the sheath 2.

Figure 3:
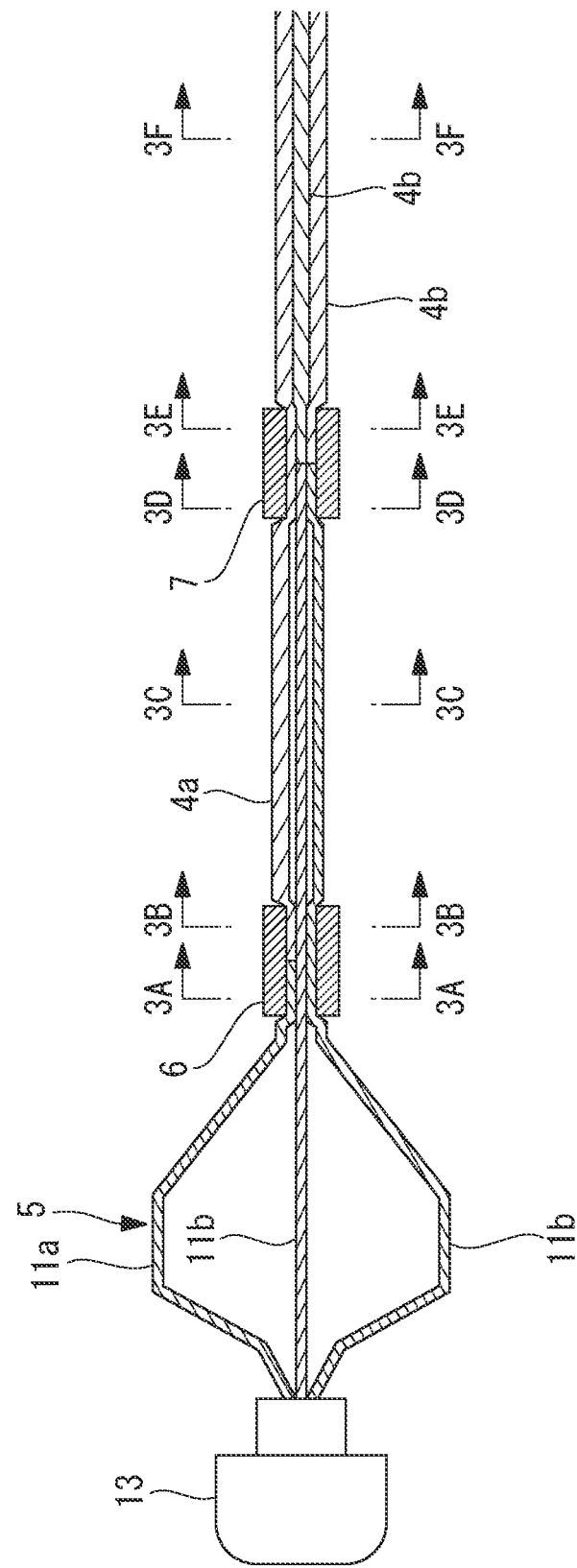
FIG. 3 is a partial longitudinal sectional view showing connection parts for the basket and the operation wires of the endoscopic treatment tool shown in FIG. 1.

The four operation wires 4a and 4b are included (three of them are shown in FIG. 3) and are respectively formed of stainless wires of the same material.

Figure 10:
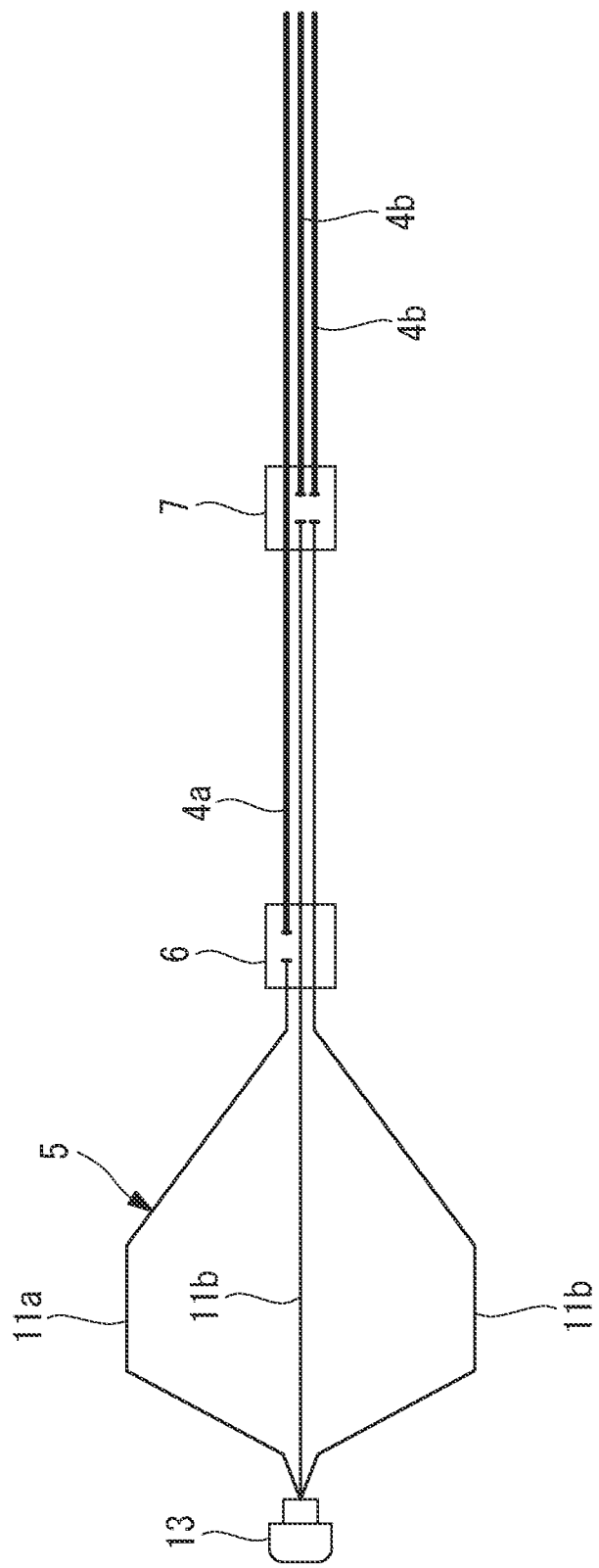
FIG. 10 is a schematic view of the endoscopic treatment tool shown in FIG. 3.

As shown in FIGS. 3 and 10, among the four operation wires 4a and 4b, the single operation wire 4a passes through the second joint part 7, a distal-end section thereof terminates at the first joint part 6, and distal-end sections of the other three operation wires 4b terminate at the second joint part 7.

In the basket 5, distal ends of the four elastic wires (three of them are shown in FIG. 3) 11a and 11b, which are respectively formed so as to be bent, are united by a distal-end tip 13, and proximal ends thereof are united by the first joint part 6, whereby a basket shape is formed between the distal-end tip 13 and the first joint part 6. The respective elastic wires 11a and 11b are formed of NiTi-alloy wires (superelastic wires) of the same material.

As shown in FIGS. 3 and 10, among the four elastic wires 11a and 11b, a proximal-end section of the single elastic wire (first wire rod) 11a terminates at the first joint part 6, the other three elastic wires (second wire rods) 11b pass through the first joint part 6, and proximal-end sections thereof terminate at the second joint part 7.

The first joint part 6 and the second joint part 7 are metal tubes and join the operation wires 4a and 4b and the elastic wires 11a and 11b that are in a state of being disposed therein, with compressive forces for radially compressing the wires (as in so-called swaging).

Figure 4:
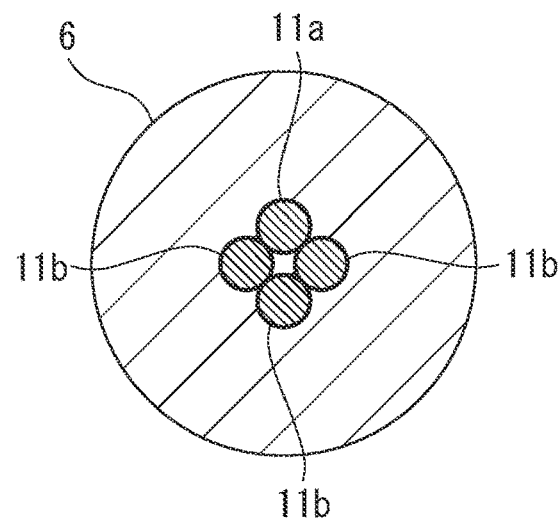
FIG. 4 is a transverse sectional view showing a cross section cut along the line 3A-3A of FIG. 3.
Figure 5:
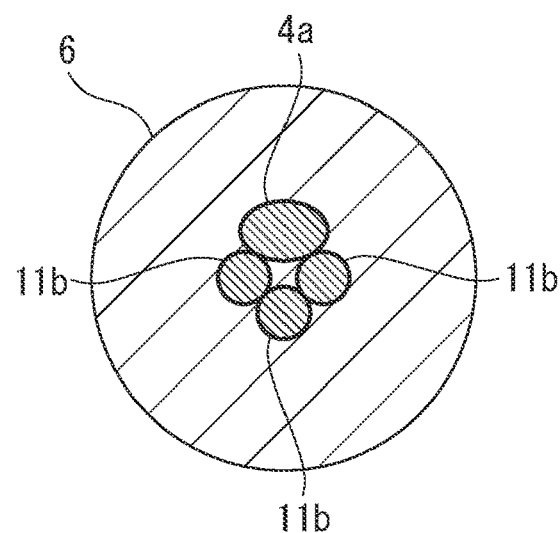
FIG. 5 is a transverse sectional view showing a cross section cut along the line 3B-3B of FIG. 3.
Figure 6:
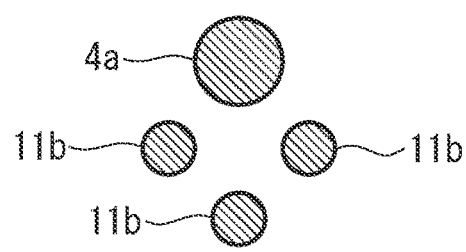
FIG. 6 is a transverse sectional view showing a cross section cut along the line 3C-3C of FIG. 3.

Specifically, in the first joint part 6, as shown in FIG. 4, the four elastic wires 11a and 11b are radially tightened inside the metal tube, and, as shown in FIG. 5, the single operation wire (first operation wire) 4a and the three elastic wires 11b are radially tightened inside the metal tube, whereby the proximal-end section of the single elastic wire (first wire rod) 11a and the distal-end section of the single operation wire (first operation wire) 4a are joined to each other. As shown in FIG. 6, the three elastic wires 11b and the single operation wire 4a extend in parallel between the first joint part 6 and the second joint part 7.

Figure 7:
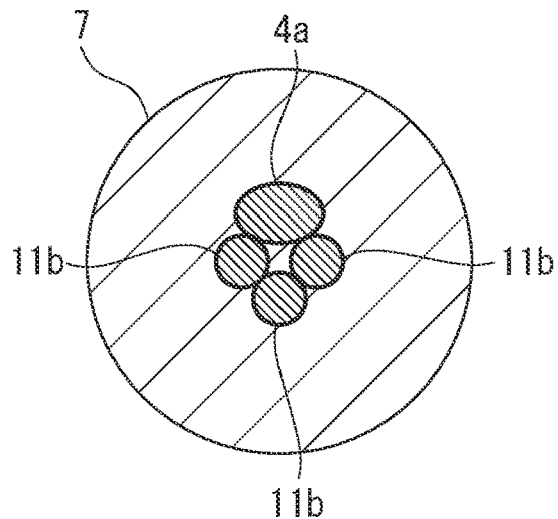
FIG. 7 is a transverse sectional view showing a cross section cut along the line 3D-3D of FIG. 3.
Figure 8:
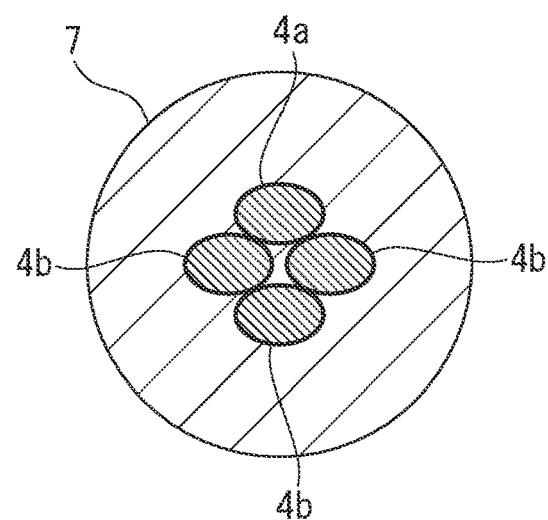
FIG. 8 is a transverse sectional view showing a cross section cut along the line 3E-3E of FIG. 3.
Figure 9:
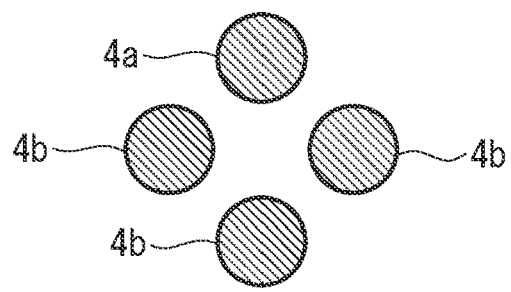
FIG. 9 is a transverse sectional view showing a cross section cut along the line 3F-3F of FIG. 3.

Furthermore, in the second joint part 7, as shown in FIG. 7, the single operation wire 4a and the three elastic wires 11b are radially tightened inside the metal tube, and, as shown in FIG. 8, the four operation wires 4a and 4b are radially tightened inside the metal tube, whereby the proximal-end sections of the three elastic wires (second wire rods) 11b and the distal-end sections of the three operation wires (second operation wires) 4b are respectively joined to each other. As shown in FIG. 9, the four operation wires 4a and 4b extend in parallel at a region closer to the proximal end than the second joint part 7 is.

As shown in FIG. 1, the operation part 3 includes: an operation-part body 14 to which the proximal end of the sheath 2 is detachably attached; and a handle 15 that is rotatably supported by the operation-part body 14.

A rack-and-pinion mechanism (not shown) is accommodated inside the operation-part body 14.

The specific configuration of the operation part 3 is the same as that disclosed in Japanese Unexamined Patent Application, Publication No. 2006-314715.

The proximal ends of the four operation wires 4a and 4b are fixed to a rack gear that constitutes the rack and pinion mechanism, and the handle 15 is fixed to a pinion gear. The handle 15 is rotated with respect to the operation-part body 14 to rotate the pinion gear and to linearly move the rack gear, which is engaged with the pinion gear, thereby making it possible to apply a pulling force to the four operation wires 4a and 4b, which are fixed to the rack gear.

The operation of the endoscopic treatment tool 1 of this embodiment will be described below.

Note that, although a description will be given below of an example case in which a gallstone X formed inside a bile duct Y is crushed, the treatment target site is not limited to the bile duct Y.

Figure 11:
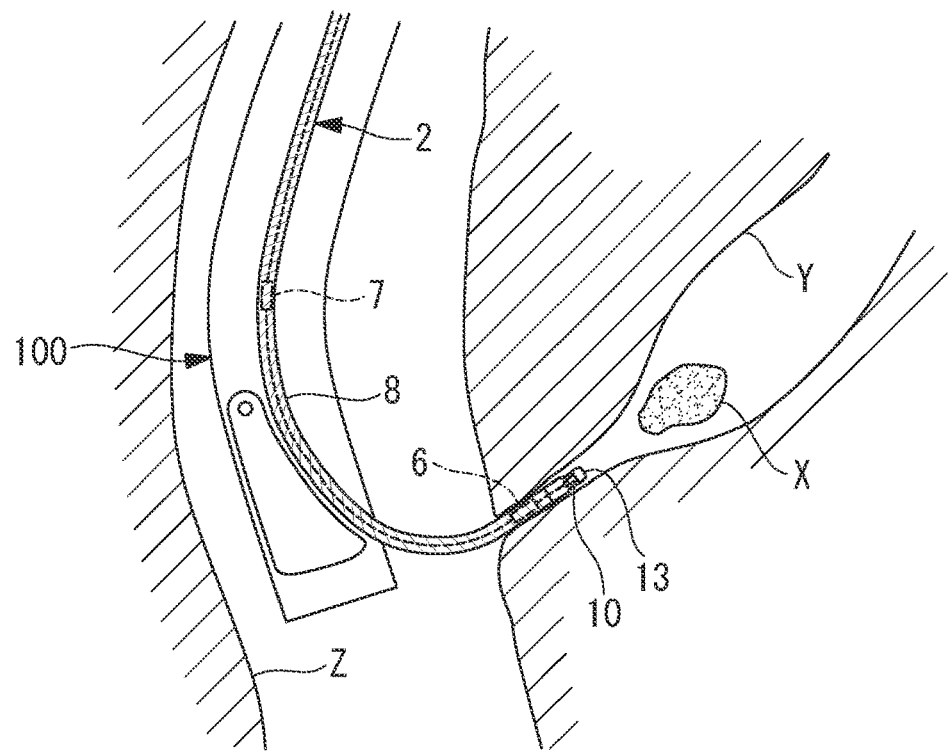
FIG. 11 is a schematic view showing a state in which the distal end of the sheath of the endoscopic treatment tool shown in FIG. 1 is inserted into the bile duct.

The endoscopic treatment tool 1 in which the elastic wires 11a and 11b, which constitute the basket 5, and the operation wires 4a and 4b have been accommodated inside the sheath 2 is inserted into the channel of the endoscope 100, passes through the channel of the endoscope 100 inserted into a duodenum Z, and is made to protrude from a side section of the distal end of the endoscope 100. Accordingly, the distal-end tip 13 is made to obliquely approach a papilla in the duodenum Z, and the distal-end tip 13 and the sheath 2 are made to enter the bile duct Y from the papilla, as shown in FIG. 11.

Figure 12:
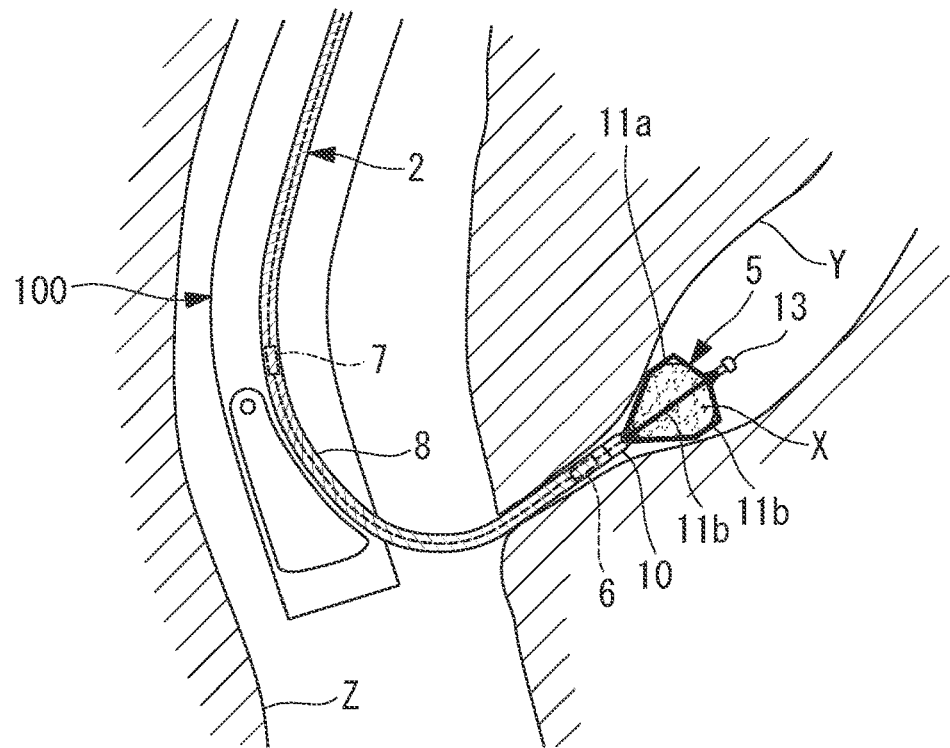
FIG. 12 is a schematic view showing a state in which the basket is opened from the state of FIG. 11 to capture a gallstone.

From this state, the operation wires 4a and 4b are moved toward the distal end in the longitudinal direction to make the basket 5 protrude from the distal end of the sheath 2, thus letting the basket 5 expand in the bile duct Y, and, as shown in FIG. 12, the gallstone X in the bile duct Y is taken into the basket 5. After the gallstone X is taken thereinto, the handle 15 is rotated with respect to the operation-part body 14 to withdraw sections of the elastic wires 11a and 11b, which constitute the basket 5, into the sheath 2, thus making the basket 5 shrink to hold the gallstone X.

In this state, the handle 15 is further rotated to increase the pulling force to be applied to the operation wires 4a and 4b, whereby the gallstone X is sandwiched between the elastic wires 11a and 11b, which constitute the basket 5, and the distal-end cover 10, which is provided at the distal end of the sheath 2, and is tightened. Because the coil sheath 8 is a dense winding, and the metal distal-end cover 10 is provided at the distal-end section thereof, the tightening force at the operation part 3 is transmitted to the elastic wires 11a and 11b, which constitute the basket 5, and the gallstone X is tightened and crushed by the basket 5.

In this case, when the gallstone X is crushed, even if an excessive force is applied to the operation wires 4a and 4b, and swaging of the first joint part 6 or the second joint part 7 is ruined, the basket 5 can be reliably prevented from falling off from the operation wires 4a and 4b. Specifically, because the three elastic wires 11b pass through the first joint part 6, and the single operation wire 4a passes through the second joint part 7, the connection state is maintained by the elastic wires 11b or the operation wire 4a even if any of the first joint part 6 and the second joint part 7 is broken.

According to the endoscopic treatment tool 1 of this embodiment, because superelastic wires made of NiTi alloy are adopted as the elastic wires 11a and 11b, which constitute the basket 5, even if an excessive force is applied thereto when the gallstone X is crushed, the elastic wires 11a and 11b can be prevented from being plastically deformed. Accordingly, in a case in which, after the gallstone X is crushed, the basket 5 is opened to collect the crushed gallstone X, or in other cases, there is an advantage in that the function of the basket 5 to smoothly expand and shrink to take the gallstone X thereinto can be maintained.

Furthermore, according to the endoscopic treatment tool 1 of this embodiment, because at least some of the wires disposed between the first joint part 6 and the second joint part 7 are formed of the elastic wires 11b, which constitute the basket 5, there is an advantage in that the bending rigidity between the first joint part 6 and the second joint part 7 is suppressed, thus making it possible to smoothly move a bending section and a forceps elevator of the endoscope 100, compared with a case in which all of the wires disposed therebetween are formed of the operation wires 4a and 4b.

Figure 13:
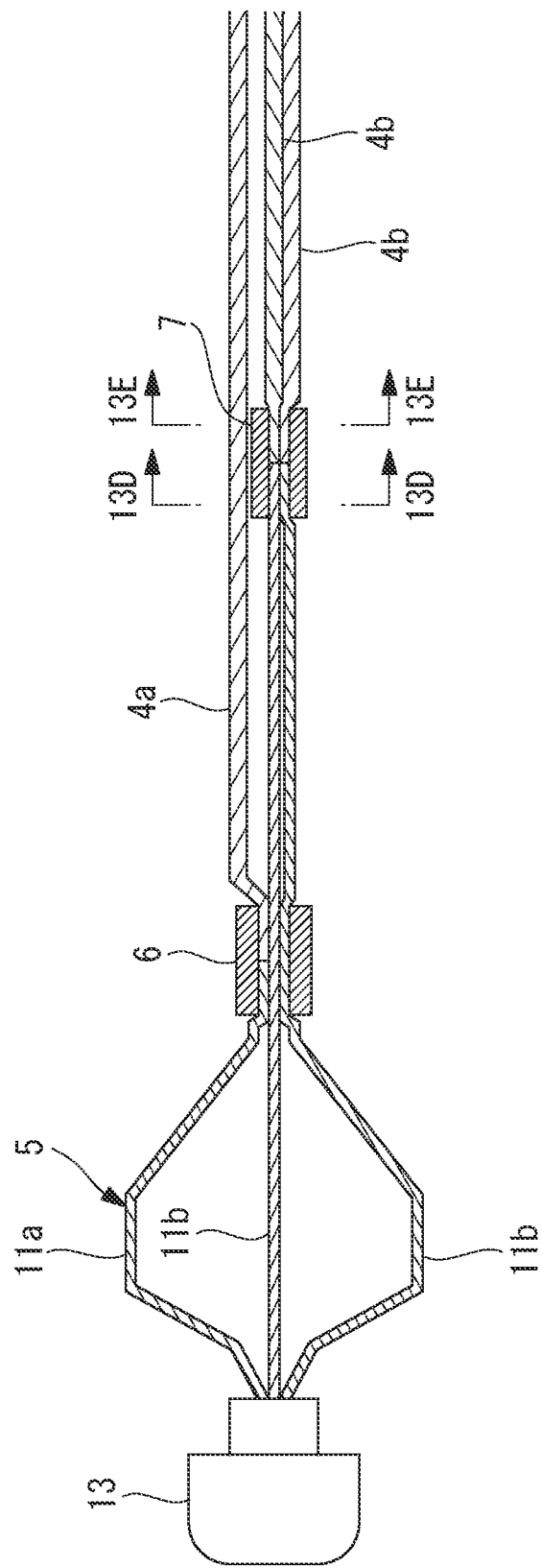
FIG. 13 is a partial longitudinal sectional view showing a first modification of the endoscopic treatment tool shown in FIG. 1.
Figure 16:
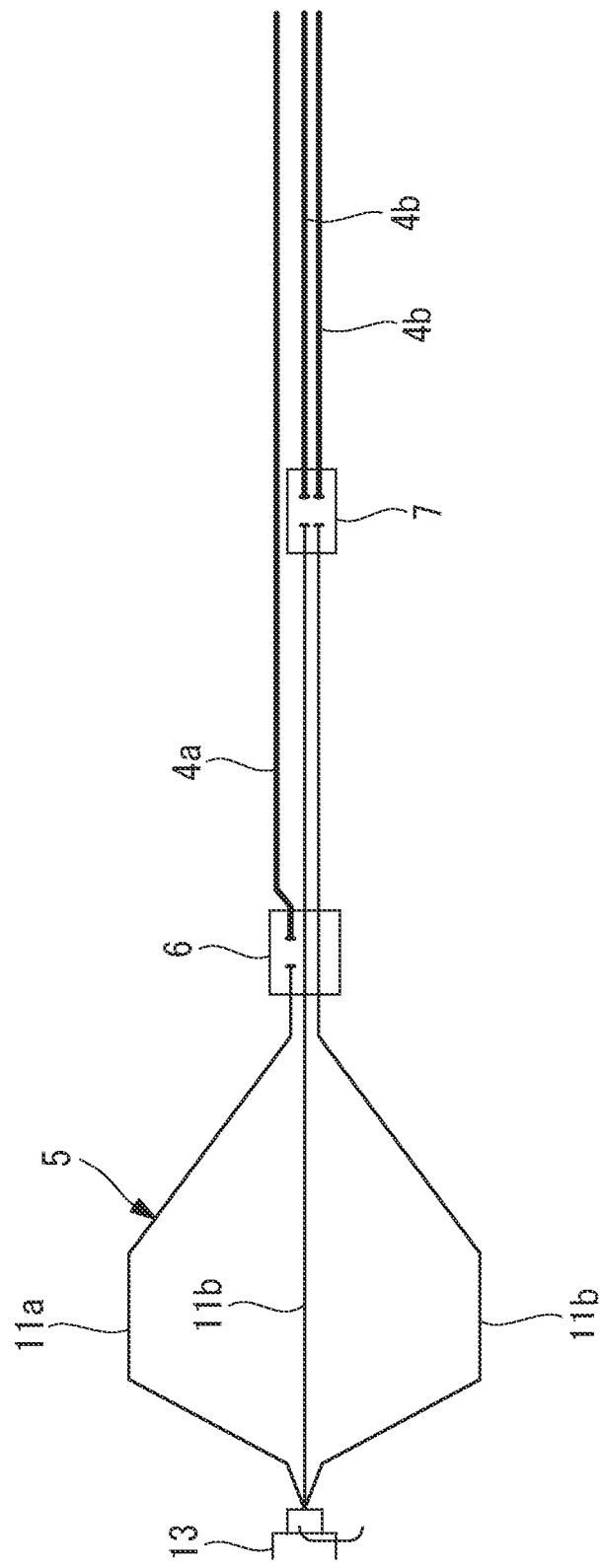
FIG. 16 is a schematic view of an endoscopic treatment tool shown in FIG. 13.

Note that, in this embodiment, although a description has been given of an example case in which the elastic wires 11b, which pass through the first joint part 6, and the operation wire 4a, which passes through the second joint part 7, all pass inside the metal tube that forms the first joint part 6 or the second joint part 7, instead of this, as shown in FIGS. 13 and 16, any of the wires may pass outside the metal tube.

Figure 14:
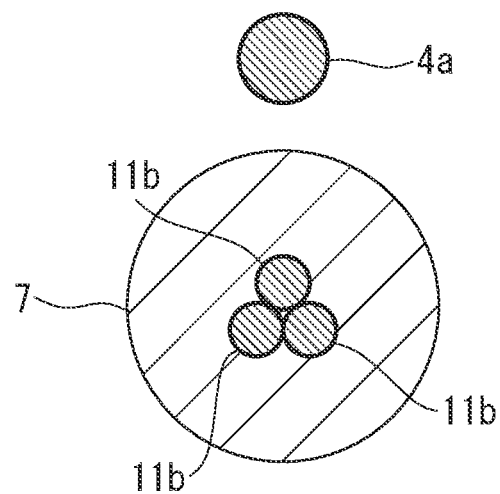
FIG. 14 is a transverse sectional view showing a cross section cut along the line 13D-13D of FIG. 13.
Figure 15:
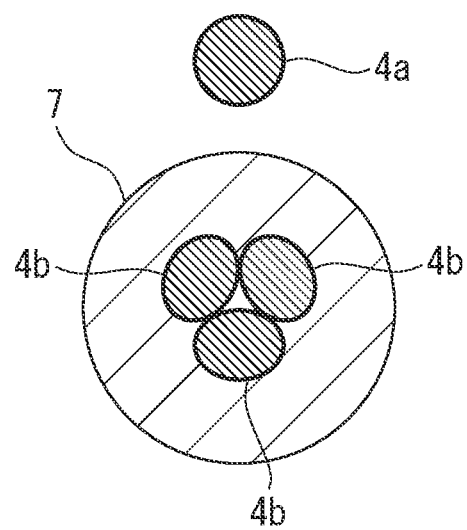
FIG. 15 is a transverse sectional view showing a cross section cut along the line 13E-13E of FIG. 13.

In this case, transverse cross sections in the second joint part 7 are shown in FIGS. 14 and 15, instead of those shown in FIGS. 7 and 8.

Figure 17:
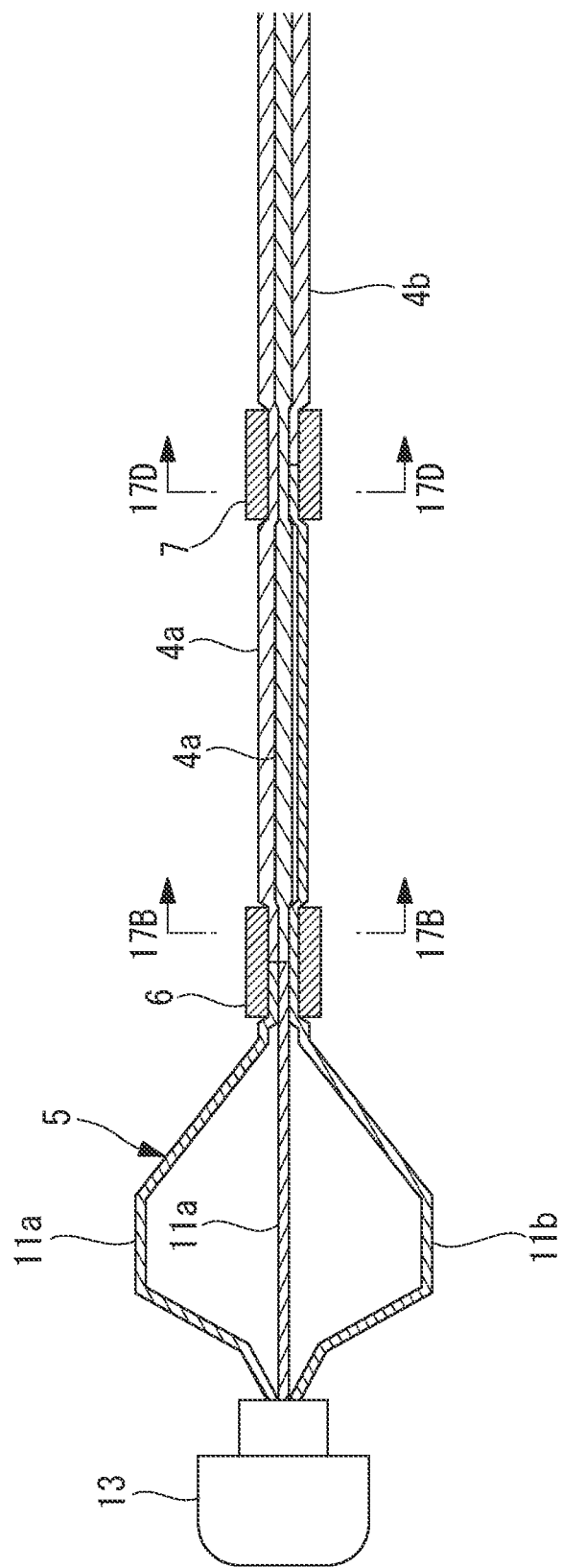
FIG. 17 is a partial longitudinal sectional view showing a second modification of the endoscopic treatment tool shown in FIG. 1.
Figure 18:
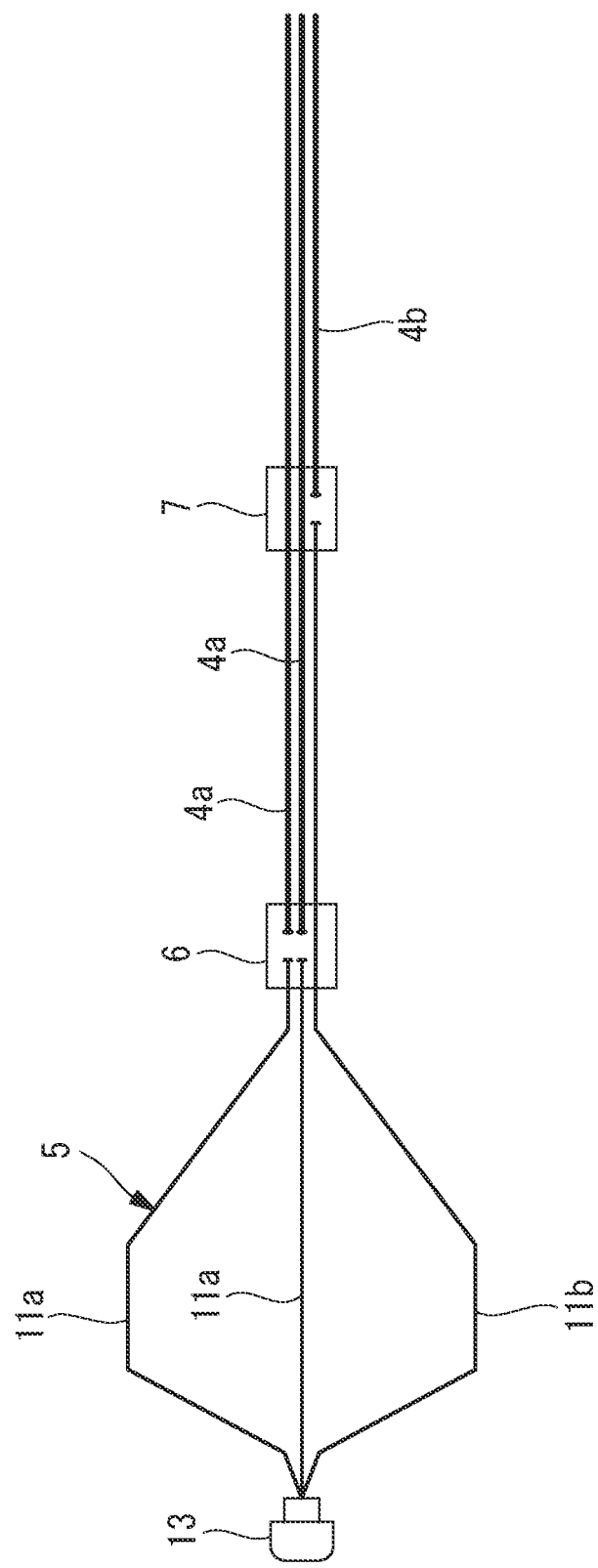
FIG. 18 is a schematic view of an endoscopic treatment tool shown in FIG. 17.
Figure 19:
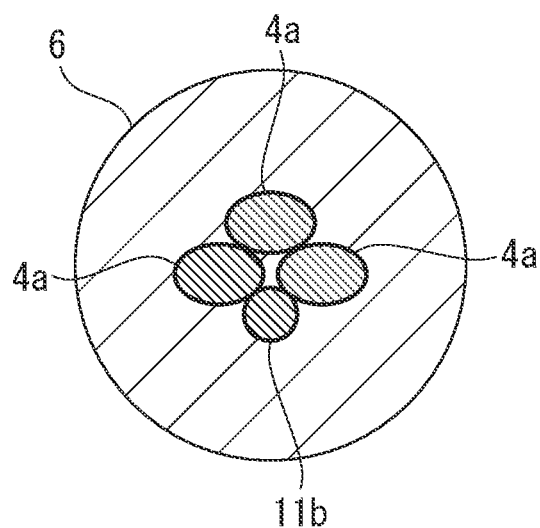
FIG. 19 is a transverse sectional view showing a cross section cut along the line 17B-17B of FIG. 17.
Figure 20:
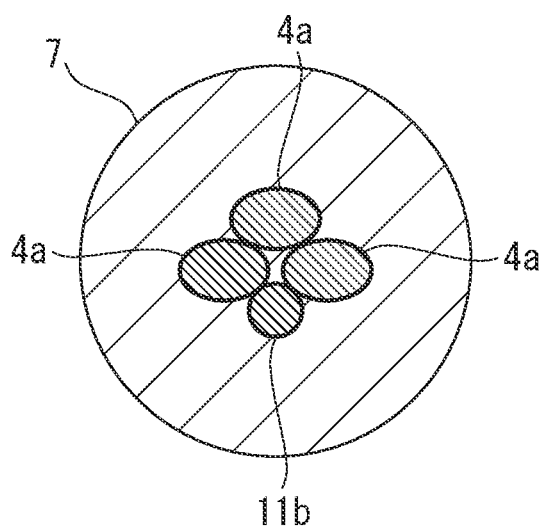
FIG. 20 is a transverse sectional view showing a cross section cut along the line 17D-17D of FIG. 17.
Figure 21:
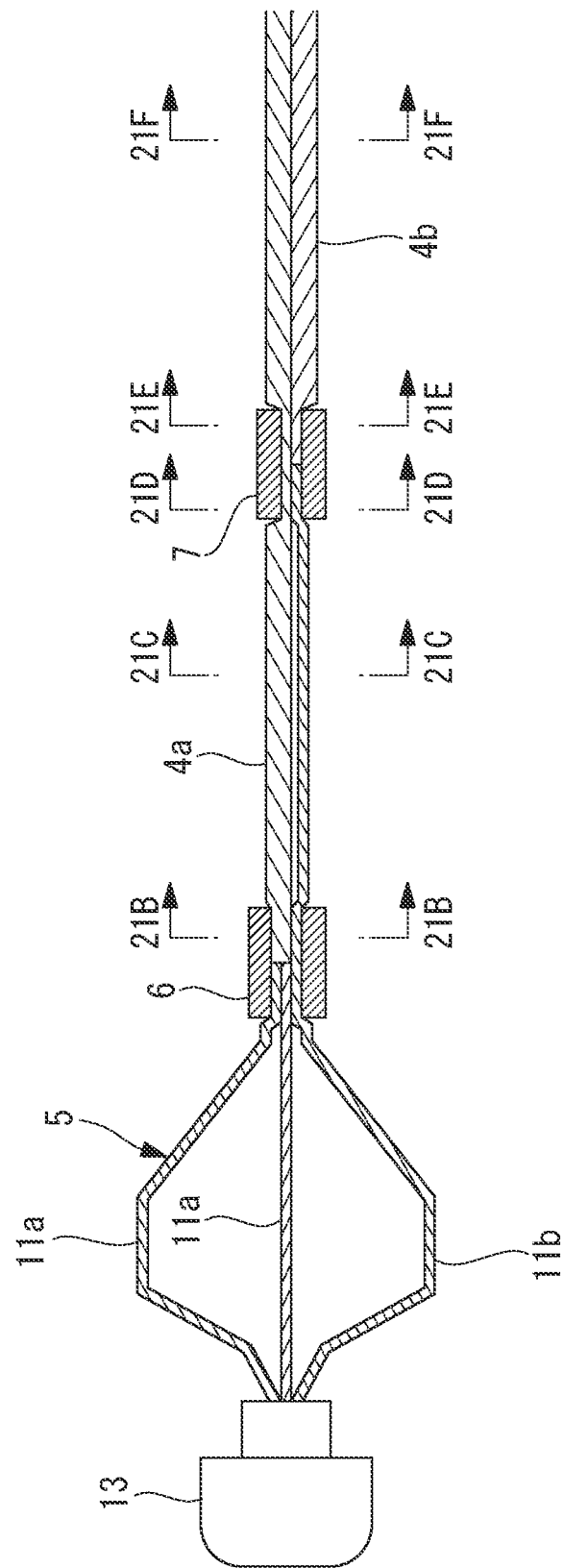
FIG. 21 is a partial longitudinal sectional view showing a third modification of the endoscopic treatment tool shown in FIG. 1.
Figure 22:
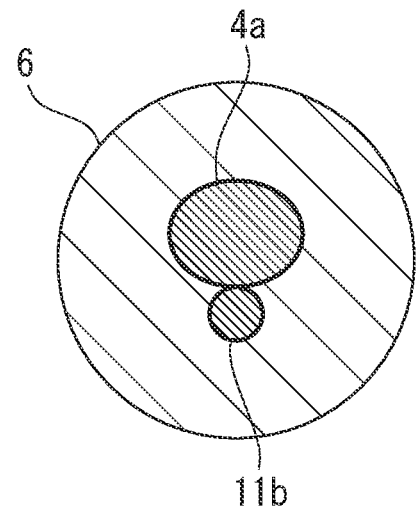
FIG. 22 is a transverse sectional view showing a cross section cut along the line 21B-21B of FIG. 21.
Figure 23:
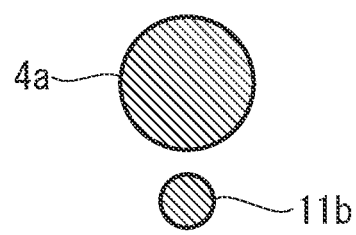
FIG. 23 is a transverse sectional view showing a cross section cut along the line 21C-21C of FIG. 21.
Figure 24:
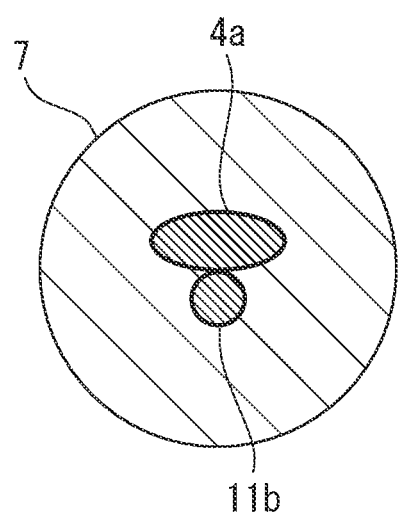
FIG. 24 is a transverse sectional view showing a cross section cut along the line 21D-21D of FIG. 21.
Figure 25:
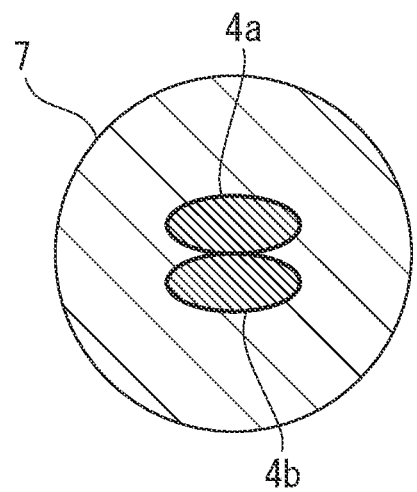
FIG. 25 is a transverse sectional view showing a cross section cut along the line 21E-21E of FIG. 21.
Figure 26:
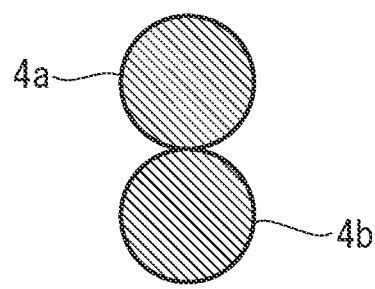
FIG. 26 is a transverse sectional view showing a cross section cut along the line 21F-21F of FIG. 21.

Furthermore, in this embodiment, although the three elastic wires 11b pass through the first joint part 6, instead of this, for example, as shown in FIGS. 17 to 19, at least one of the elastic wires 11b may pass through the first joint part 6. Furthermore, although the single operation wire 4a passes through the second joint part 7, instead of this, one or more, for example, three as shown in FIG. 20, operation wires 4a may pass through the second joint part 7.

Furthermore, in this embodiment, although the four operation wires 4a and 4b are formed of wires of the same material, instead of this, it is also possible to adopt, as the operation wire 4a, which passes through the second joint part 7, a wire having rigidity equal to or less than the elastic wires constituting the basket 5.

In this case, the number of operation wires 4a made to pass through the second joint part 7 can be freely selected within the range in which the total number of operation wires 4a and elastic wires 11b to be joined in the second joint part 7 becomes equal to the number of the elastic wires 11a and 11b, which constitute the basket 5.

Accordingly, it is possible to further reduce the bending rigidity between the first joint part 6 and the second joint part 7 and to further facilitate the movement of the bending section and the forceps elevator of the endoscope 100.

Furthermore, as shown in FIGS. 21 to 26, it is also possible to set the number of operation wires 4a made to pass through the second joint part 7 to one and to adopt an operation wire 4a that has rigidity equivalent to the three elastic wires 11a and 11b, which constitute the basket 5.

Furthermore, in the configuration shown in FIG. 17, among the four operation wires 4a and 4b, it is also possible to adopt, as one of the three operation wires 4a that pass through the second joint part 7, a wire that has higher rigidity than one of the elastic wires 11a and 11b, which constitute the basket 5, and that has lower rigidity than the operation wire 4b that does not pass through the first joint part 6.

In this case, the number of operation wires 4a made to pass through the second joint part 7 can be freely selected within the range in which the total number of operation wires 4a and elastic wires 11b to be joined in the second joint part 7 becomes equal to the number of the elastic wires 11a and 11b, which constitute the basket 5.

Accordingly, it is possible to further reduce the bending rigidity between the first joint part 6 and the second joint part 7 and to improve the rigidity of the operation wires 4a and 4b at a region closer to the proximal end than the second joint part 7 is, thus making force transmission favorable.

As a result, the above-described embodiment leads to the following aspects.

One aspect of the present invention is directed to an endoscopic treatment tool including: a sheath that has a longitudinal axis; a first operation wire and a second operation wire that are inserted through the sheath so as to be able to be moved forward and backward; a treatment part constituted by a first wire rod and a second wire rod that have lower bending rigidity than bending rigidity of the second operation wire; a first joint part inside which the second wire rod passes and that joins a distal-end section of the first operation wire and a proximal-end section of the first wire rod; and a second joint part that joins a distal-end section of the second operation wire and a proximal-end section of the second wire rod.

According to this aspect, because the first joint part joins the first wire rod and the first operation wire, and the second wire rod is made to pass through the first joint part, even if a large force is applied to the treatment part, the first joint part is broken, and the joint between the first wire rod and the first operation wire is separated, the connection state is maintained by the second wire rod. Furthermore, because the second joint part joins the second wire rod and the second operation wire, the second wire rod and the second operation wire are separated if the second joint part is broken; however, the connection state is maintained by the first operation wire, which extends up to the first joint part. Accordingly, the treatment part can be prevented from falling off.

Specifically, the treatment part can be prevented from falling off even when a joining method with low joining strength is used in the joint parts, and an increase in the cost can be suppressed even when wire rods of an expensive material are used because the wire rods, which constitute the treatment part, do not extend toward the proximal end beyond the second joint part.

Another aspect of the present invention is directed to an endoscopic treatment tool including: a sheath that has a longitudinal axis; a first operation wire and a second operation wire that are inserted through the sheath so as to be able to be moved forward and backward; a treatment part constituted by a first wire rod and a second wire rod that have lower bending rigidity than bending rigidity of the second operation wire; a first joint part that joins a distal-end section of the first operation wire and a proximal-end section of the first wire rod; and a second joint part inside which the first operation wire passes and that joins a distal-end section of the second operation wire and a proximal-end section of the second wire rod.

According to this aspect, because the first joint part joins the first wire rod and the first operation wire, even if a large force is applied to the treatment part, the first joint part is broken, and the joint between the first wire rod and the first operation wire is separated, the connection state is maintained by the second wire rod, which extends up to the second joint part. Furthermore, because the second joint part joins the second wire rod and the second operation wire, the second wire rod and the second operation wire are separated if the second joint part is broken; however, the connection state is maintained by the first operation wire, which extends up to the first joint part. Accordingly, the treatment part can be prevented from falling off.

Specifically, the treatment part can be prevented from falling off even when a joining method with low joining strength is used in the joint parts, and an increase in the cost can be suppressed even when wire rods of an expensive material are used because the wire rods, which constitute the treatment part, do not extend toward the proximal end beyond the second joint part.

In the above-described aspect, the first operation wire may pass through an inner side of the second joint part.

With this configuration, as in the first joint part, in which three kinds of wires or rods, that is, the first wire rod, the second wire rod, and the first operation wire are tied up, three kinds of wires or rods, that is, the first operation wire, the second operation wire, and the second wire rod are tied up in the second joint part.

In the above-described aspect, the second wire rod may pass through an inner side of the first joint part.

With this configuration, as in the second joint part, in which three kinds of wires or rods, that is, the second wire rod, the first operation wire, and the second operation wire are tied up, three kinds of wires or rods, that is, the first wire rod, the second wire rod, and the first operation wire are tied up in the first joint part.

In the above-described aspect, the first joint part and the second joint part may be metal tubes; in a state of being inserted into the first joint part, the distal-end section of the first operation wire and the proximal-end section of the first wire rod may be joined to each other by a compressive force for radially compressing the first joint part; and, in a state of being inserted into the second joint part, the distal-end section of the second operation wire and the proximal-end section of the second wire rod may be joined to each other by a compressive force for radially compressing the second joint part.

With this configuration, in the first joint part, the distal-end section of the first operation wire and the proximal-end section of the first wire rod are radially compressed in a state of being inserted into the metal tube, thereby being joined. In the second joint part, the distal-end section of the second operation wire and the proximal-end section of the second wire rod are radially compressed in a state of being inserted into the metal tube, thereby being joined. Accordingly, the operation wire and the wire rod of different materials can be easily joined.

In the above-described aspect, the first wire rod and the second wire rod may be made of the same material.

In the above-described aspect, the treatment part may be a basket.

In the above-described aspect, the first wire rod and the second wire rod may be made of NiTi alloy, and the first operation wire and the second operation wire may be made of stainless steel.

With this configuration, the treatment part can be prevented from plastically deformed even if a large force is applied thereto while being used, and a larger force can be applied to the first operation wire and the second operation wire, which have high rigidity.

According to the present invention, an advantageous effect is afforded in that it is possible to prevent a treatment part from falling off from an operation wire while suppressing the cost even when the treatment part is formed by using wires of a material that suppresses plastic deformation.

REFERENCE SIGNS LIST 1 endoscopic treatment tool
2 sheath
4a operation wire (first operation wire)
4b operation wire (second operation wire)
5 basket (treatment part)
6 first joint part
7 second joint part
11a elastic wire (first wire rod)
11b elastic wire (second wire rod)

The invention claimed is:
1. An endoscopic treatment tool comprising:
a first wire;
a second wire;
a treatment part comprising:
  a first rod; and
  a second rod, the first rod and the second rod each having a lower bending rigidity than a bending rigidity of the second wire;
a first joint configured to join a distal-end section of the first wire, a proximal-end section of the first rod and a portion of the second rod that are in a state of being disposed therein, with compressive forces for radially compressing the distal-end section of the first wire, the proximal-end section of the first rod and the portion of the second rod; and
a second joint located proximally relative to the first joint and configured to join a distal-end section of the second wire and a proximal-end section of the second rod that are in a state of being disposed therein, with compressive forces for radially compressing the distal-end section of the second wire and the proximal-end section of the second rod,
wherein the first wire passes through the second joint, and
wherein the second rod passes through the first joint.

2. The endoscopic treatment tool according to claim 1, wherein the first rod and the second rod are made of a same material.

3. The endoscopic treatment tool according to claim 1, wherein the first rod and the second rod comprise a wire, and
wherein the treatment part comprises a basket.

4. The endoscopic treatment tool according to claim 1, wherein the first rod and the second rod are made of NiTi alloy, and the first wire and the second wire are made of stainless steel.

5. The endoscopic treatment tool according to claim 1, wherein a length of the first wire is longer than a length of the second wire.

6. The endoscopic treatment tool according to claim 1, wherein the first joint is configured to tie the first rod, the second rod and the first wire.

7. The endoscopic treatment tool according to claim 1, wherein the second joint is configured to tie the first wire, the second wire and the second rod.

8. The endoscopic treatment tool according to claim 1, further comprising a sheath,
wherein the first wire and the second wire are inserted through the sheath.

9. The endoscopic treatment tool according to claim 1, wherein the first wire passes through an inner side of the second joint.

10. The endoscopic treatment tool according to claim 1, wherein the first joint and the second joint are metal tubes.

11. The endoscopic treatment tool according to claim 1, wherein the second joint is configured to join the distal-end section of the second wire, the proximal-end section of the second rod and a portion of the first wire that are in a state of being disposed therein, with compressive forces for radially compressing the distal-end section of the second wire, the proximal-end section of the second rod and the portion of the first wire.

12. The endoscopic treatment tool according to claim 1, wherein the bending rigidity of each of the first rod and the second rod is lower than a bending rigidity of the first wire.

13. The endoscopic treatment tool according to claim 12, wherein the bending rigidity of the second wire is higher than the bending rigidity of the first wire.

14. The endoscopic treatment tool according to claim 13, wherein the second wire comprises a plurality of wires, and
wherein the second rod comprises a plurality of rods.

15. An endoscopic treatment tool comprising:
a first wire;
a second wire;
a treatment part comprising:
a first rod; and
a second rod having a lower bending rigidity than a bending rigidity of the second wire;
a first joint configured to join a distal-end section of the first wire, a proximal-end section of the first rod and a portion of the second rod that are in a state of being disposed therein, with compressive forces for radially compressing the distal-end section of the first wire, the proximal-end section of the first rod and the portion of the second rod; and
a second joint located proximally relative to the first joint and configured to join a distal-end section of the second wire and a proximal-end section of the second rod that are in a state of being disposed therein, with compressive forces for radially compressing the distal-end section of the second wire and the proximal-end section of the second rod,
wherein the first wire extends from the first joint toward a proximal end of endoscopic treatment tool, and
wherein the second rod extends from a distal end of the treatment part toward the second joint and passes through the first joint.

16. The endoscopic treatment tool according to claim 15, wherein the first wire does not switch to another wire at a position corresponding to the second joint.

17. The endoscopic treatment tool according to claim 15, wherein a length of the first wire is longer than a length of the second wire.

18. The endoscopic treatment tool according to claim 15, wherein the first wire passes through the second joint.

19. The endoscopic treatment tool according to claim 15, wherein the second joint is configured to join the distal-end section of the second wire, the proximal-end section of the second rod and a portion of the first wire that are in a state of being disposed therein, with compressive forces for radially compressing the distal-end section of the second wire, the proximal-end section of the second rod and the portion of the first wire.

* * * * *